(12) United States Patent
Harris et al.

(10) Patent No.: US 7,786,439 B2
(45) Date of Patent: Aug. 31, 2010

(54) DETECTOR APPARATUS

(75) Inventors: Andrew Roland Harris, Seaview Downs (AU); Michael Francis Edwards, Glenunga (AU); Kenneth Graham Smith, Wayville (AU); Gavin Leith Christie, Golden Grove (AU); Nick John Deans, Woodcroft (AU)

(73) Assignee: Scantech International Pty Ltd., Camden Park, South Australia (AU)

( * ) Notice: Subject to any disclaimer, the term of this patent is extended or adjusted under 35 U.S.C. 154(b) by 0 days.

(21) Appl. No.: 11/870,677

(22) Filed: Oct. 11, 2007

(65) Prior Publication Data

US 2008/0217537 A1 Sep. 11, 2008

Related U.S. Application Data

(63) Continuation of application No. PCT/AU2006/000558, filed on Apr. 28, 2006.

(60) Provisional application No. 60/676,214, filed on Apr. 29, 2005.

(30) Foreign Application Priority Data

Apr. 28, 2005 (AU) ............... 2005902147

(51) Int. Cl.
*G01T 1/34* (2006.01)
(52) U.S. Cl. .................... 250/336.1
(58) Field of Classification Search ............. 250/336.1, 250/338.5, 339.03, 339.07
See application file for complete search history.

(56) References Cited

U.S. PATENT DOCUMENTS

| | | | | |
|---|---|---|---|---|
| 4,090,074 A | * | 5/1978 | Watt et al. ............ | 378/88 |
| 4,632,807 A | * | 12/1986 | Marsoner ............ | 422/82.08 |
| 4,649,483 A | * | 3/1987 | Dixon, Jr. ............ | 702/12 |
| 4,916,719 A | * | 4/1990 | Kawatra et al. ......... | 378/46 |
| 5,179,580 A | * | 1/1993 | Komatani et al. ........ | 378/44 |
| 5,210,419 A | * | 5/1993 | Buheitel ............ | 250/362 |
| 5,235,190 A | | 8/1993 | Tucker et al. | |
| 5,297,420 A | * | 3/1994 | Gilliland et al. ......... | 73/38 |
| 6,130,931 A | | 10/2000 | Laurila et al. | |
| 6,342,701 B1 | * | 1/2002 | Kash ............ | 250/458.1 |
| 6,421,415 B1 | * | 7/2002 | Peczkis et al. ......... | 378/46 |
| 6,567,498 B1 | | 5/2003 | Troxler et al. | |

(Continued)

FOREIGN PATENT DOCUMENTS

DE 3627449 A1 2/1988

(Continued)

OTHER PUBLICATIONS

International Search Report by Australian Patent Office dated Jul. 13, 2006.

*Primary Examiner*—David P Porta
*Assistant Examiner*—Djura Malevic
(74) *Attorney, Agent, or Firm*—Hamre, Schumann, Mueller & Larson, P.C.

(57) ABSTRACT

A detector apparatus is disclosed. In one embodiment, the detector apparatus includes i) a radiation detector configured to generate an analog signal representative of radiation incident upon the radiation detector and ii) an analog-to-digital converter configured to convert the analog signal to a corresponding digital signal, wherein the radiation detector and the analog-to-digital converter are both housed in a common temperature-controlled housing.

17 Claims, 2 Drawing Sheets

U.S. PATENT DOCUMENTS

| | | | |
|---|---|---|---|
| 2003/0227998 A1* | 12/2003 | Liao | 378/98.8 |
| 2004/0195676 A1 | 10/2004 | Quarre | |
| 2005/0094466 A1* | 5/2005 | Archer et al. | 365/222 |
| 2005/0117698 A1 | 6/2005 | Lacey et al. | |
| 2005/0123093 A1* | 6/2005 | Lawaczeck et al. | 378/98.11 |
| 2005/0127300 A1* | 6/2005 | Bordynuik | 250/361 R |
| 2007/0235828 A1* | 10/2007 | Yoshihara et al. | 257/432 |

FOREIGN PATENT DOCUMENTS

| | | |
|---|---|---|
| EP | 933624 A1 | 8/1999 |

* cited by examiner

DETECTOR APPARATUS

RELATED APPLICATIONS

This application is a continuation application, and claims the benefit under 35 U.S.C. §§120 and 365 of PCT Application No. PCT/AU2006/000558, filed on Apr. 28, 2006, which is hereby incorporated by reference. The PCT application also claimed priority from U.S. Provisional Application No. 60/676,214, filed on Apr. 29, 2005 and Australian Patent Application No. 2005902147 filed on Apr. 28, 2005, both of which are hereby incorporated by reference.

BACKGROUND OF THE INVENTION

1. Field of the Invention

The present invention relates to a detector apparatus for use in analyzing material travelling along a conveyor.

2. Description of the Related Technology

A detector apparatus is known which includes a radiation source arranged to be positioned beneath a conveyor belt and a housing at an end of a C-frame for holding a detector above the conveyor belt. A cabinet is provided on an upright member of the C-frame for housing electronics in the form of a multi-channel analyzer and computer processing equipment. Wiring extends from the detector to within the cabinet, for providing analog signals to the multi-channel analyzer, for subsequent processing. In order to achieve reliable scan results, the detector needs to be maintained within a preferred temperature range, as does at least the multi-channel analyzer within the cabinet.

SUMMARY OF CERTAIN INVENTIVE ASPECTS

One aspect of the present invention provides a detector apparatus including a detector housing which houses a radiation detector and a multi-channel analyzer coupled thereto.

In one embodiment, input contacts of the analyzer are coupled directly to output contacts of the detector.

In one embodiment, a common temperature control assembly is used to monitor and control temperature within the housing. In one embodiment, the temperature control assembly includes a temperature sensor positioned adjacent the detector.

In one embodiment, the analyzer is arranged to output a digital signal. In one embodiment, the digital signal is transmitted from the housing along a cable connected to processing equipment of the apparatus. The processing equipment may be provided in a cabinet arranged in spaced location relative to the housing.

In one embodiment, the apparatus is for analyzing ash content of coal.

Another aspect of the present invention provides a detector apparatus including i) a radiation detector for generating an analog signal representative of radiation incident upon the radiation detector, and ii) an analog-to-digital converter for converting the analog signal to a corresponding digital signal, wherein the radiation detector and the analog-to-digital converter are both housed in a common temperature-controlled housing.

Still another aspect of the present invention provides a detector apparatus comprising: i) means for generating an analog signal representative of radiation incident upon the generating means and ii) means for converting the analog signal to a corresponding digital signal, wherein the generating means and the converting means are both housed in a common temperature-controlled housing.

BRIEF DESCRIPTION OF THE DRAWINGS

Embodiments of the invention will be described with reference to the accompanying drawings.

DESCRIPTION OF CERTAIN INVENTIVE EMBODIMENTS

Figure 1:
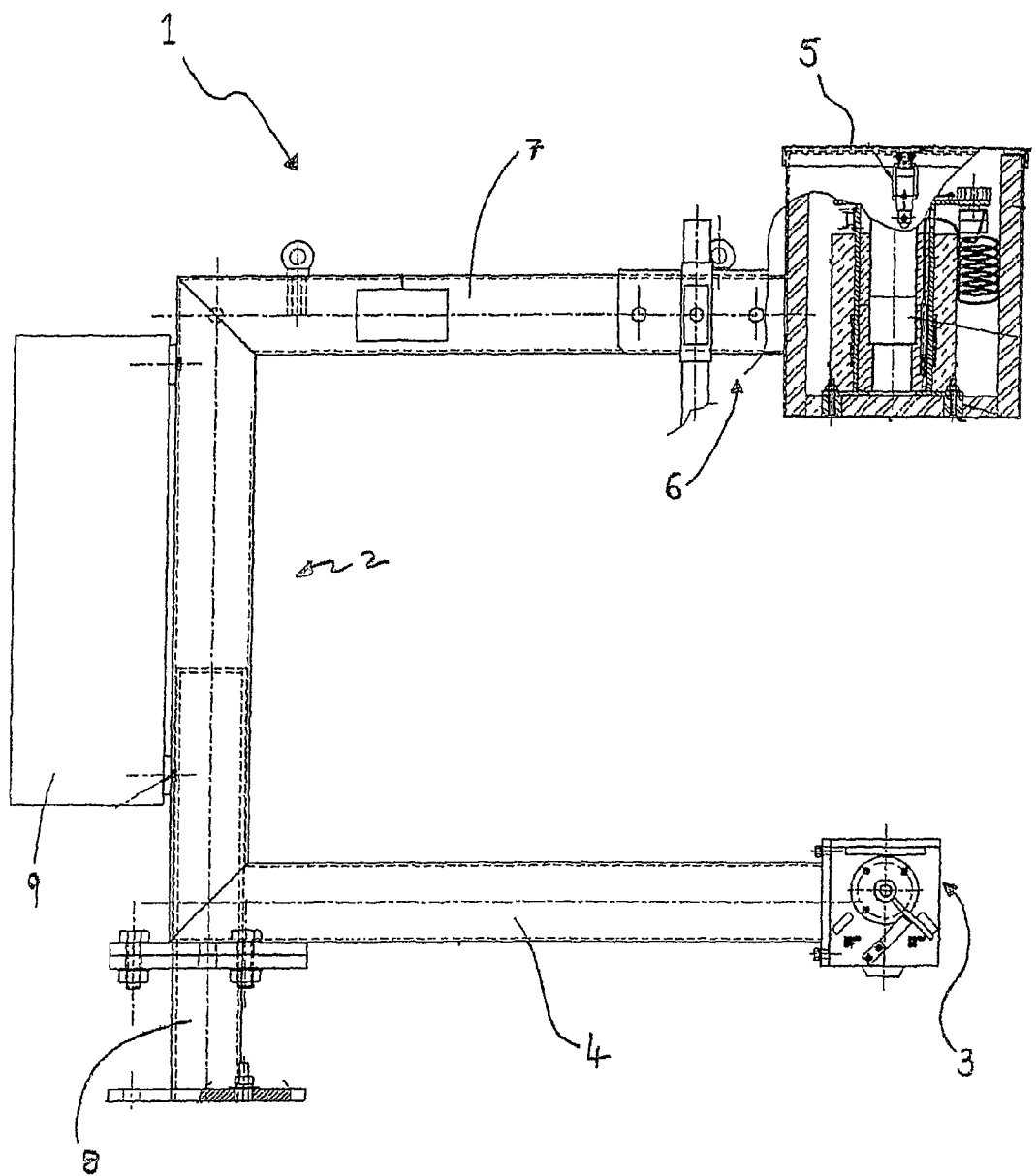
FIG. 1 is a diagrammatic perspective view of a detector system according to one embodiment of the invention.

With regard to FIG. 1, a detector apparatus 1 is shown as including a C-shaped support frame 2 with a radiation source 3 in a foot 4 of the frame 2 and a housing 5 suspended above the source 3 at a free end 6 of an upper arm 7 of the frame 2. An upright member 8 of the frame 2 supports a cabinet 9 which houses processing equipment (not shown) in the form of a microprocessor and the like. In use, the frame 2 is positioned so that the radiation source 3 and housing 5 are located above and below a conveyor belt (not shown) which passes therebetween, in order to analyze material, such as coal, carried by the belt.

Figure 2:
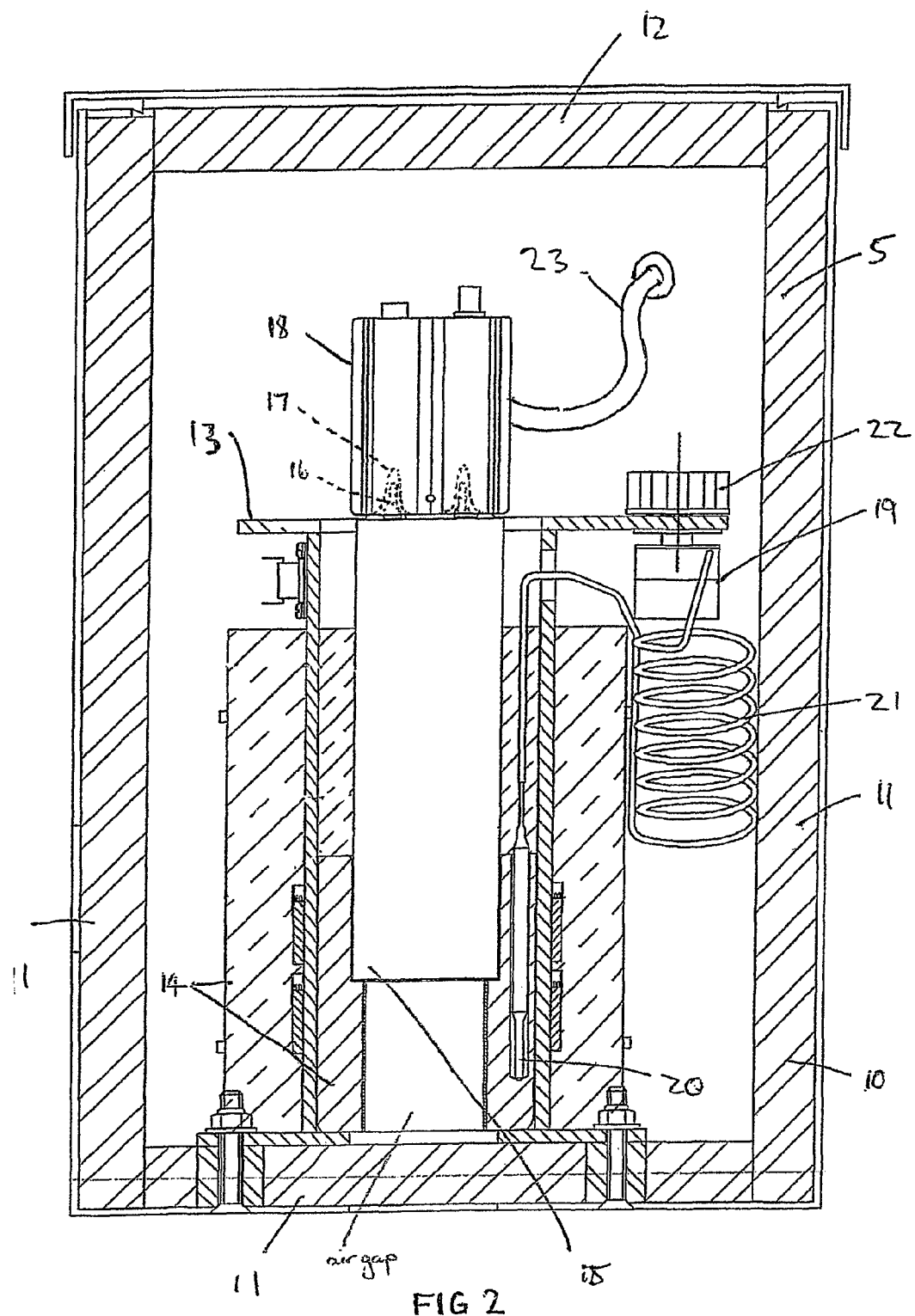
FIG. 2 is a cross-sectional view of a housing of the system shown in FIG. 1.

Referring now to FIG. 2, the housing 5 is shown in cross section as including a base component 10 with insulating wall panels 11 and an insulated lid component 12. A mounting structure 13 is screw fitted relative to the base component 10. The mounting structure 13 has further insulating material 14 surrounding a detector 15, which is positioned to receive incident radiation from the radiation source 3. The detector 15 has a number of output contacts 16 which are in direct connection to input contacts 17 of a multi-channel analyzer 18 that is fitted directly above the detector 15. A thermal control assembly 19 is also mounted to the structure 13 and includes a temperature sensor 20 which is embedded in the material 14 surrounding the detector 15 and is thermally coupled via a coil 21 to a temperature setting dial 22. Accordingly, the temperature of both the detector 15 and the analyzer 18 may be monitored and set at a suitable operating temperature.

The analyzer 18 is configured to convert the analog signals from the output contacts 16 of the detector 15 to a digital output signal which is transmitted along an output cable 23 that runs externally of the housing and into the cabinet 9.

As such, the apparatus 1 presents an advantage in so far as providing for temperature control of both the detector and analyzer in a single housing, which will in turn reduce control systems, required circuitry and componentry, as compared to the known form of detector system. In addition, the use of a digital output from the housing 5, further simplifies wiring into the cabinet 9 and obviates the need to provide shielding to the wiring, which was required with the analog signals used with the prior art.

In an alternative embodiment, the component 18 shown in FIG. 2 is a standard analog-to-digital converter (ADC) that converts analog signals from the detector 15 into corresponding digital signals that are sent on output cable 23 from the housing 5 to the cabinet 9 where they are processed by the processing equipment located therein to provide the remaining multi-channel analyzer functions that enable standard spectral analysis of the detector output. In one embodiment, the processing equipment in the cabinet 9 includes a standard computer system such as an Intel® IA-32 computer system having a standard digital interface board, and the multi-channel analyzer functions are provided by software modules stored on non-volatile storage associated with the processing equipment. Thus the combination of the ADC 18 located in the housing 5 and the processing equipment located in the cabinet 9 can together be considered to constitute or include a multi-channel analyzer. By locating both the detector 15 and the ADC 18 in a common temperature-controlled housing 5, the stability and accuracy of the detector apparatus 1 is enhanced.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

The invention claimed is:

1. A detector apparatus comprising:
   a radiation detector positioned to detect radiation incident on the radiation detector;
   a multi-channel analyzer to analyze output of the radiation detector and having input contacts directly coupled to output contacts of the radiation detector;
   an insulated housing that houses the radiation detector and the multi-channel analyzer; and
   a temperature control assembly configured to monitor and control temperature within the housing.

2. The detector apparatus of claim 1, further comprising a support frame supporting the housing in an upper arm of the frame and a radiation source in a foot of the frame to transmit radiation through a material carried between the source and the detector.

3. The detector apparatus of claim 2, further comprising a cabinet supported by an upright member of the frame and housing processing equipment to process an output of the multi-channel analyzer.

4. The detector apparatus of claim 1, wherein the detector is positioned within insulating material of a mounting structure mounted in the housing.

5. The detector apparatus of claim 1, wherein the multi-channel analyzer and the detector are in mutual abutment.

6. The detector apparatus of claim 1, wherein a base of the housing comprises insulating material so that radiation incident on a detecting face of the detector passes from a radiation source external of the housing through the insulating material.

7. The detector apparatus of claim 1, wherein the housing comprises a base component with insulating wall panels and an insulated lid component.

8. The detector apparatus of claim 1, wherein the temperature control assembly includes a temperature sensor positioned adjacent to the detector.

9. The detector apparatus of claim 8, wherein the temperature sensor is embedded in insulating material surrounding the detector.

10. The detector apparatus of claim 1, wherein the multi-channel analyzer is configured to receive an analog input signal from the radiation detector and to output a digital signal.

11. The detector apparatus of claim 10, wherein the digital signal is transmitted from the housing along a cable connected to a processing component of the apparatus.

12. The detector apparatus of claim 1, further comprising a processing component configured to process the digital signal to generate spectral data representative of the radiation incident upon the radiation detector.

13. The detector apparatus of claim 12, wherein the processing component is provided in a cabinet arranged in spaced location relative to the housing.

14. The detector apparatus of claim 1, wherein the apparatus is configured to analyze ash content of coal.

15. The detector apparatus of claim 1, wherein the radiation detector and the multi-channel analyzer directly contact each other.

16. The detector apparatus of claim 1, further comprising a support frame supporting the housing in the frame and a radiation source in the frame to transmit radiation through a material carried between the source and the detector.

17. The detector apparatus of claim 16, further comprising a cabinet supported by the frame and housing processing equipment to process an output of the multi-channel analyzer.

* * * * *